(12) United States Patent
Muller et al.

(10) Patent No.: US 11,559,390 B2
(45) Date of Patent: Jan. 24, 2023

(54) CORNEAL IMPLANT SYSTEMS AND METHODS

(71) Applicant: Allotex, Inc., Boston, MA (US)

(72) Inventors: David Muller, Boston, MA (US); Michael Mrochen, Eglisau (CH); Siran Wang, Maynard, MA (US); Zhiyi Yuan, Medford, MA (US); Sara Correia, Zürich (CH); Daniel Boss, Zürich (CH)

(73) Assignee: Allotex, Inc., Boston, MA (US)

( * ) Notice: Subject to any disclaimer, the term of this patent is extended or adjusted under 35 U.S.C. 154(b) by 0 days.

(21) Appl. No.: 16/347,115

(22) PCT Filed: Oct. 29, 2018

(86) PCT No.: PCT/US2018/058035
§ 371 (c)(1),
(2) Date: May 2, 2019

(87) PCT Pub. No.: WO2019/084557
PCT Pub. Date: May 2, 2019

(65) Prior Publication Data
US 2020/0253720 A1    Aug. 13, 2020

Related U.S. Application Data

(60) Provisional application No. 62/578,388, filed on Oct. 27, 2017.

(51) Int. Cl.
*A61F 2/14* (2006.01)
*A61F 9/008* (2006.01)

(52) U.S. Cl.
CPC .......... *A61F 2/1451* (2015.04); *A61F 2/148* (2013.01); *A61F 9/00827* (2013.01); *A61F 9/00831* (2013.01); *A61F 9/00834* (2013.01); *A61F 2009/00872* (2013.01); *A61F 2009/00895* (2013.01); *A61F 2009/00897* (2013.01)

(58) Field of Classification Search
CPC combination set(s) only.
See application file for complete search history.

(56) References Cited

U.S. PATENT DOCUMENTS

| | | | |
|---|---|---|---|
| 10,092,393 B2* | 10/2018 | Muller | A61F 9/0081 |
| 2009/0326650 A1* | 12/2009 | Zickler | A61F 2/1451 |
| | | | 606/5 |
| 2014/0264980 A1* | 9/2014 | Muller | A61F 2/142 |
| | | | 264/1.36 |

* cited by examiner

*Primary Examiner* — Nathan J Jenness
(74) *Attorney, Agent, or Firm* — McDonnell Boehnen Hulbert & Berghoff LLP

(57) ABSTRACT

An example method for cutting a plurality of lenticules from a donor cornea includes receiving a donor cornea, cutting a first layer of a first set of lenticules from the donor cornea, and cutting a second layer of a second set of lenticules from the donor cornea. The lenticules are cut according to a pattern that to maximizes the number of lenticules, thereby maximizing the number of implants from the single donor cornea. An example implant handling device includes a body. The body includes a flattened end configured to receive a corneal implant and keep the corneal implant from rolling or folding. The flattened end has a width and a height, the width being greater than the height. The body includes a slit opening to the flattened end, the slit opening configured to allow the corneal implant to pass into the flattened end.

5 Claims, 2 Drawing Sheets

CORNEAL IMPLANT SYSTEMS AND METHODS

CROSS-REFERENCE TO RELATED APPLICATIONS

This application is a National Stage Application of International Patent Application No. PCT/US2018/058035, filed Oct. 29, 2018, which claims priority to, and benefit of, U.S. Provisional Patent Application Ser. No. 62/578,388, filed Oct. 27, 2017, the contents of these applications being incorporated entirely herein by reference.

FIELD OF THE INVENTION

The present disclosure relates generally to systems and methods for correcting vision, and more particularly, to systems and methods relating to implants to reshape the cornea in order to correct vision.

BACKGROUND

A variety of eye disorders, such as myopia, hyperopia, astigmatism, and presbyopia, involve abnormal shaping of the cornea. This abnormal shaping prevents the cornea from properly focusing light onto the retina in the back of the eye (i.e., refractive error). A number of treatments attempt to reshape the cornea so that the light is properly focused. For instance, a common type of corrective treatment is LASIK (laser-assisted in situ keratomileusis), which employs a laser to reshape the cornea surgically.

SUMMARY

According to aspects of the present disclosure, embodiments employ implants to reshape the cornea in order to correct vision. For instance, such embodiments may address the refractive errors associated with eye disorders such as myopia, hyperopia, astigmatism, and presbyopia. The implants may be formed from natural tissue, such as donor corneal tissue.

According to aspects of the present disclosure, an example method for cutting a plurality of lenticules from a donor cornea includes receiving a donor cornea, cutting a first layer of a first set of lenticules from the donor cornea, and cutting a second layer of a second set of lenticules from the donor cornea. Each of the first set of lenticules and the second set of lenticules has a thickness measured along a z-axis extending through the donor cornea. The first layer and the second layer extend along an x-y plane that is transverse to the z-axis. The first layer and the second layer overlaps along the z-axis.

In the example method, the first set of lenticules and the second set of lenticules may each be substantially similar in size and shape.

In the example method, each of the first set of lenticules and the second set of lenticules may be defined by a first surface and an opposing second surface, the first surface and the second surface coming together at a periphery of the lenticule, the first surface being substantially planar and the second surface being substantially convex. In some cases, the substantially convex surfaces of the first set of lenticules in the first layer may face the substantially convex surfaces of the second set of lenticules in the second layer.

In the example method, the second set of lenticules may be positioned to overlap the first set of lenticules along the x-y plane, the second set of lenticules being centered at different (x, y) points along the x-y plane from the first set of lenticules.

In the example method, the first layer and the second layer may be cut from the donor cornea with a femtosecond laser.

According to further aspects of the present disclosure, an example implant handling device includes a body. The body includes a flattened end configured to receive a corneal implant and keep the corneal implant from rolling or folding. The flattened end has a width and a height, the width being greater than the height. The body includes a slit opening to the flattened end, the slit opening configured to allow the corneal implant to pass into the flattened end.

In the example implant handling device, the height of the flattened end may be between approximately 50 µm to approximately 100 µm. The width of the flattened end may be between approximately 4 mm to approximately 7 mm. The length of the body may be between approximately 1.5 cm to approximately 2.5 cm. The body of the implant handling device may be coupled to a syringe for applying a negative pressure or a positive pressure to the flattened end.

Figure 1A:
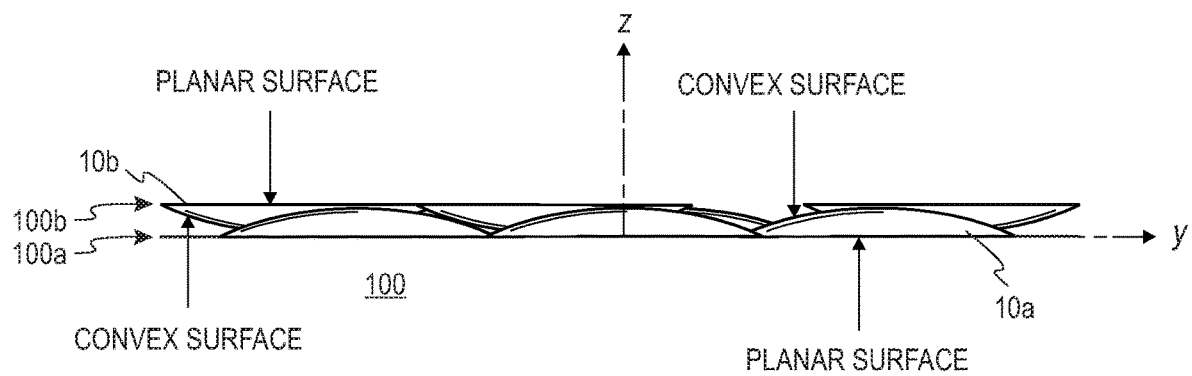
FIG. 1A illustrates a side view of an example pattern for cutting a donor cornea to yield a plurality of lenticules, according to aspects of the present disclosure.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DESCRIPTION

Example systems and methods employ implants to reshape the cornea in order to correct vision. For instance, such embodiments may address the refractive errors associated with eye disorders such as myopia, hyperopia, astigmatism, and presbyopia. Example systems and methods employ implants that are formed from natural tissue, such as donor corneal tissue.

Implants formed from donor cornea can be employed to reshape the cornea in order to correct a variety of eye disorders, such as myopia, hyperopia, astigmatism, and presbyopia. Approaches for producing and implementing such implants are described, for instance, in U.S. Patent Application Publication No. 2014/0264980, filed Jan. 10, 2014, U.S. Patent Application Publication No. 2017/0027754, filed Feb. 28, 2016, and U.S. patent application Ser. No. 15/588,249, filed May 5, 2017, the contents of these applications being incorporated entirely herein by reference.

Figure 1B:
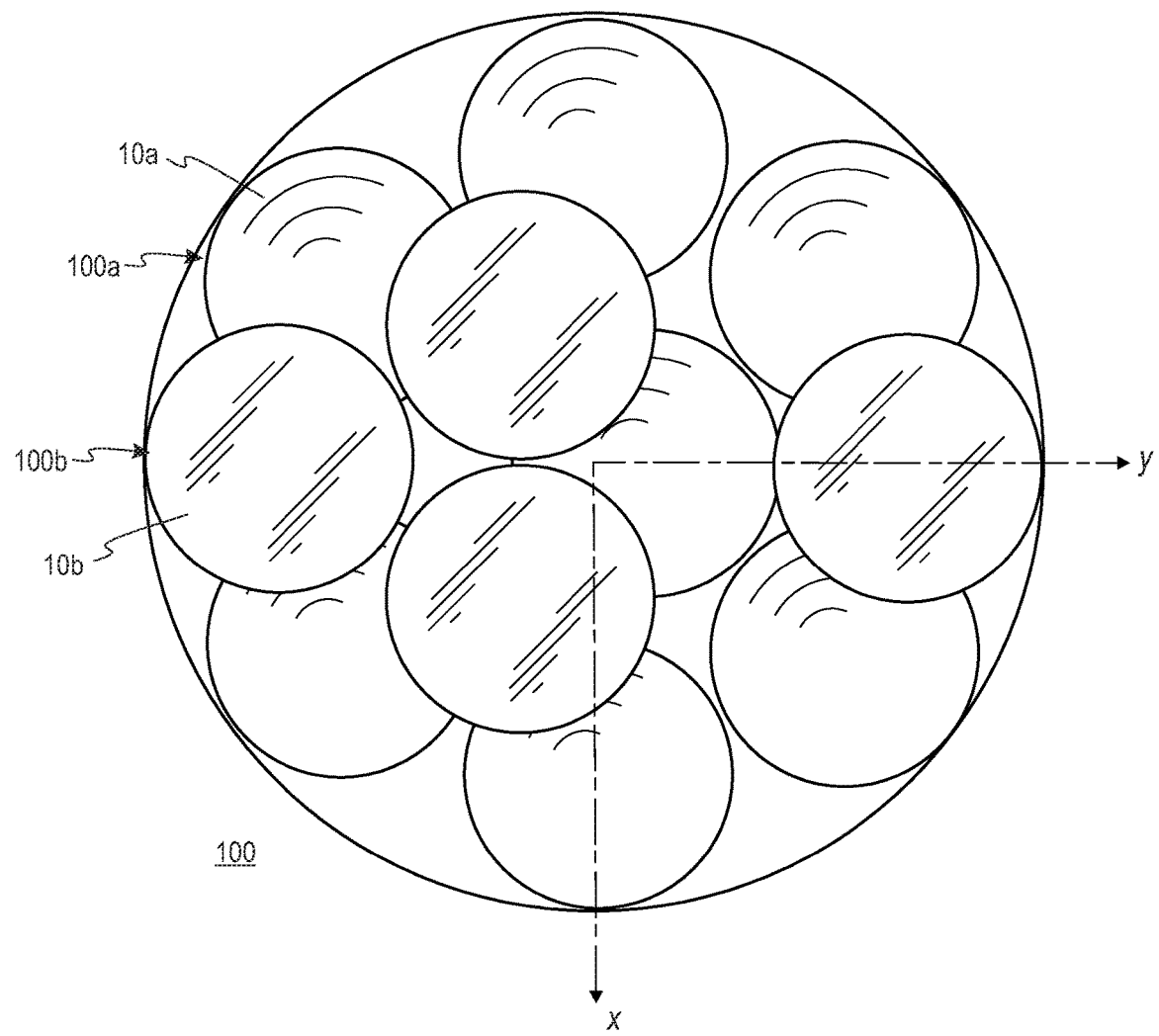
FIG. 1B illustrates a top view of the example pattern shown in FIG. 1B.

A plurality of implants can be formed by shaping lenticules that are cut from a single donor cornea. According to aspects of the present disclosure, a single donor cornea is cut to maximize the number of lenticules, thereby maximizing the number of implants from the single donor cornea. FIGS. 1A, B illustrate side and top views, respectively, of an example pattern 100 for cutting a donor cornea to yield more lenticules. FIGS. 1A, B illustrate two layers 100a and 100b of the pattern 100. The layer 100a yields a plurality of lenticules 10a, and the layer 100b yields a plurality of lenticules 10b. A femtosecond laser, for instance, may be employed to cut the lenticules 10a, b according to the pattern 100. The layer 100b overlaps the layer 100a along the z-axis as shown in FIG. 1A. The lenticules 10b are positioned to overlap the lenticules 10a along the x-v plane as shown in FIG. 1B, where the lenticules 10b are centered at different (x, y) points from the lenticules 10a.

The lenticules 10a, b are shaped to achieve the arrangement of pattern 100. The lenticules 10a, 10b are substantially similar in shape and size. In particular, each lenticule 10a, b is defined by a first surface and an opposing second surface which come together at their peripheries (i.e., a periphery of the lenticule), where the first surface is substantially planar while the second surface is substantially convex. As shown in FIG. 1A, the flat planar surfaces of the lenticules 10b face upwardly (in positive z-direction), while the flat planar surfaces of the lenticules 10a face downwardly (in negative z-direction). With the convex surfaces of the lenticules 10a, b facing each other, the lenticules 10b of the layer 100b can be cut from corneal tissue between the lenticules 10a of the layer 100a.

An alternating series of layers 100a, b can be cut from the entire thickness of the donor cornea. Accordingly, more efficient use of the donor cornea is achieved and more lenticules can be produced from a single donor cornea. For instance, if a single donor cornea is approximately 500 µm in thickness, conventional approaches can yield 128 lenticules that are approximately 3 mm in diameter and approximately 30 µm in thickness from the donor cornea. The pattern 100, however, can yield, from a similar donor cornea, 176 lenticules that are approximately 3 mm in diameter and approximately 30 µm in thickness with the shape described above. It is contemplated that variations of the pattern 100 and lenticule shapes may be employed to achieve more efficient of donor cornea.

According to other aspects of the present disclosure, producing and/or implementing implants from donor cornea take into account the fact that different parts of the cornea have different structures and different hydration characteristics. Systems and methods can track the part of the donor cornea from which each lenticule is cut. When a lenticule is cut from a particular part of a donor cornea, information on the particular part of the donor cornea is recorded and communicated, so that the lenticule can be subsequently handled according to the specific mechanical, hydration, or cutting properties of tissue from the particular part of the donor cornea.

According to further aspects of the present disclosure, lenticules are cut to form implants that have shapes that facilitate the implant procedure. For instance, in some embodiments, a femtosecond laser can be employed to shape the lenticules into biconvex implants. Due to the symmetry of a biconvex implant, a practitioner can position the implant in a recipient cornea without regard to which side of the implant faces anteriorly or posteriorly.

Figure 2:
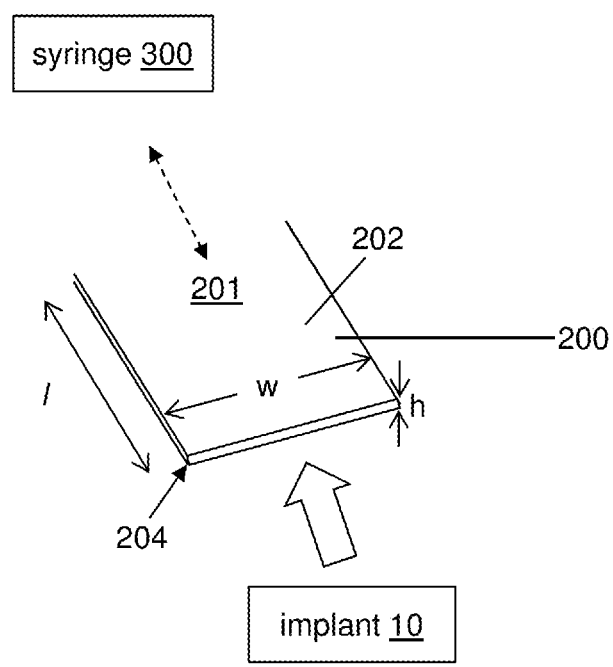
FIG. 2 illustrates an example implant handling device, according to aspects of the present disclosure.

According to aspects of the present disclosure, a specially configured implant handling device 200 facilitates implant procedures. Implants may be approximately 20 µm to approximately 50 µm in thickness. Due to the thin shape of implants, there is a need for a device that allows a surgeon to handle an implant (e.g., picking up and releasing the implant) more easily. During the implant procedure, it is preferable to keep the implant from rolling or folding up (i.e., generally flat). As such, the implant handling device 200 includes a body 201 with a flattened end 202 that receives the implant and keeps the implant from rolling or folding up. FIG. 2 provides a simplified, non-limiting illustration to demonstrate aspects of the implant handling device 200. The flattened end 202 of the body 201 may have a duck-billed or similar shape and the opening 204 is a very thin slit. The height h of the flattened end 202 of the body 201, for instance, may be approximately 50 µm to approximately 100 µm to accommodate the thickness of the implant. The implant handling device 200, in some respects, may resemble a modified Jones tube; however, at least the end 202 of the body 201 is flattened and not cylindrical in profile. In some cases, one surface of an implant may be substantially planar while the opposing surface may be substantially contoured or curved, e.g., convex. The implant handling device 200 also allows the contoured surface to face upwardly for implantation, as preferred.

In some cases, implants of varying diameters may be available. As such, different implant handling devices 200 with corresponding dimensions may also be available. For instance, implants may be available with diameters of approximately 3 mm or approximately 6 mm. Corresponding implant handling devices 200 may, therefore, have openings that have widths w of approximately 4 mm or approximately 7 mm, respectively, while the height h remains approximately 50 µm to approximately 100 µm. The dimensions thus provide for a very thin height h relative to the width w. The length l of the body 201 of the implant handling device 200 may be approximately 1.5 cm to approximately 2.5 cm.

In an example implementation, the implant may be drawn through the opening 204 into the implant handling device 200 (e.g., with negative pressure from a 3 ml syringe 300 coupled to the implant handling device 200) and then pushed from the implant handling device 200 onto a bed in the recipient cornea under a flap (e.g., with positive pressure from the syringe 300). The flattened end 202 of the implant handling device 200 keeps the implant generally flat during this process.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A method for cutting a plurality of lenticules from a donor cornea, comprising:
   receiving a donor cornea;
   cutting a first layer of a first set of lenticules from the donor cornea; and
   cutting a second layer of a second set of lenticules from the donor cornea,
   wherein each of the first set of lenticules and the second set of lenticules has a thickness measured along a z-axis extending through the donor cornea,
   the first layer and the second layer extend along an x-y plane that is transverse to the z-axis, and
   the first layer and the second layer overlap along the z-axis,
   wherein the second set of lenticules are positioned to overlap the first set of lenticules along the x-y plane, the second set of lenticules being centered at different (x, y) points along the x-y plane from the first set of lenticules.

2. The method of claim 1, wherein the first set of lenticules and the second set of lenticules are equal in size and shape.

3. The method of claim 1, wherein each of the first set of lenticules and the second set of lenticules is defined by a first surface and an opposing second surface, the first surface and the second surface coming together at a periphery of the lenticule, the first surface being planar and the second surface being convex.

4. The method of claim 3, wherein the convex surfaces of the first set of lenticules in the first layer face the convex surfaces of the second set of lenticules in the second layer.

5. The method of claim 1, wherein the first layer and the second layer are cut from the donor cornea with a femtosecond laser.

\* \* \* \* \*